United States Patent [19]

Paparizos et al.

[11] Patent Number: 4,877,898

[45] Date of Patent: Oct. 31, 1989

[54] PROCESS FOR ONE STEP ESTERIFICATION USING AN INTERMETALLIC PALLADIUM BASED CATALYST SYSTEM

[75] Inventors: Christos Paparizos, Willowick; Wilfrid G. Shaw, Lyndhurst; James L. Callahan, Wooster, all of Ohio

[73] Assignee: The Standard Oil Company, Cleveland, Ohio

[21] Appl. No.: 873,428

[22] Filed: Jun. 12, 1986

Related U.S. Application Data

[63] Continuation of Ser. No. 724,533, Apr. 18, 1985, abandoned.

[51] Int. Cl.$^4$ .............................................. C07C 67/39
[52] U.S. Cl. ................................... 560/208; 560/100; 560/102; 560/103; 560/104; 560/105; 560/106; 560/109; 560/112; 560/113; 560/131; 560/238
[58] Field of Search ................ 560/208, 238, 100, 102, 560/103, 104, 106, 109, 112, 113, 131, 105; 502/307, 329, 349

[56] References Cited

U.S. PATENT DOCUMENTS 3,772,383 11/1973 Kominami et al. .............. 260/479 R
4,107,204 8/1978 Murib .............................. 260/530 N
4,124,633 11/1978 Leonard et al. ...................... 562/598
4,249,019 2/1981 Tamura et al. ...................... 560/208
4,520,125 5/1985 Baer et al. ........................... 502/170

FOREIGN PATENT DOCUMENTS 1433168 4/1976 United Kingdom .
2051056 6/1983 United Kingdom .

Primary Examiner—Donald B. Moyer
Assistant Examiner—L. Hendriksen
Attorney, Agent, or Firm—M. F. Esposito; J. E. Miller; L. W. Evans

[57] ABSTRACT

A process for the one step esterification of aldehydes and alcohols comprises the steps of combining an aldehyde with an alcohol, in the presence of oxygen and in contact with a catalyst having the general formula $$PdTe_aZn_dE_e$$

where

E is one or more metals from the group consisting of group IA, IIA, IVA, VIIB or VIII metals, As or Sb; and a, d and e are from about 0 to 3 with the proviso that at least d or e≠0.

9 Claims, No Drawings

PROCESS FOR ONE STEP ESTERIFICATION USING AN INTERMETALLIC PALLADIUM BASED CATALYST SYSTEM

This application is a continuation of application Ser. No. 724,533, filed Apr. 18, 1985 now abandoned.

TECHNICAL FIELD

Many different processes, including those that are two-step, together with varied catalyst systems, have been utilized heretofore to esterify aldehydes such as, for example, methacrolein with alcohols.

The present invention is directed to an esterification process for the direct one-step conversion of aldehydes and alcohols to the corresponding ester, this process being one conducted in the presence of oxygen and with a palladium based intermetallic catalyst.

BACKGROUND ART

U.S. Pat. No. 4,107,204 provides a three step process for the oxidation of propylene to acrylic acid in the presence of a palladium catalyst and acetic acid. The catalyst employed is a supported palladium-copper or palladium-silver two metal compound.

U.K. Pat. No. 1,433,168, owned by the Assignee of record, is directed toward a one step process for the preparation of acrylate and methacrylate esters from unsaturated aldehydes over known catalysts comprising molybdenum, vanadium and tungsten. The feature of the invention is the addition of alcohol directly to the oxidation reaction, so that it is present with at least some of the aldehyde.

British Pat. No. 2,051,056 discloses a method for preparing carboxylic esters by reacting an aldehyde with an alcohol in the presence of a catalyst comprising palladium and bismuth and optionally an alkali metal or alkaline earth metal or other metal. The catalyst is prepared by chemically reducing a soluble palladium salt to palladium metal while the bismuth is present either in a metallic state or as a bismuth compound such that the two components interact with each other.

The foregoing methods, although relevant to the process of the present invention, would not lead one skilled in that art to the process of this invention, which employs specific palladium based catalysts, and the significant advantages resulting from the practice thereof.

DISCLOSURE OF THE INVENTION

The present invention is directed to the one-step esterification of aldehydes and alcohols comprising the steps of combining an aldehyde with an alcohol, in the presence of oxygen, and in contact with a palladium based catalyst of the formula $$PdTe_aZn_dE_e$$

where
E is one or more metals from the group consisting of IA, IIA, IVA, IB, VIIB or VIII metals, As or Sb; and
a, d and e are from about 0 to 3, with the proviso that at least d or e$\neq$0.

These catalysts can be used unsupported or supported. The operating temperature can range from about 20° C. about 200° C., with the preferred range being 35° to 80° C. The oxygen pressure can range from subatmospheric to about 20 atm, with the preferred range being atmospheric to 10 atm. The alcohol to aldehyde ratio can range from about 1:1 to 50:1 with the preferred range being 2 to 20:1.

PREFERRED MODE FOR CARRYING OUT THE INVENTION

In the practice of this invention, an aldehyde such as acrolein, butyraldehyde or methacrolein is converted to its corresponding ester, in the presence of oxygen, with an alcohol such as methanol or ethanol, together with the intermetallic palladium based catalyst system utilized in the practice of this invention. The invention process is a one-step process that produces esters under mild conditions and achieves a significant per pass conversion percent.

Other aldehydes that can be employed include saturated aliphatic aldehydes having between 1 to 12 carbon atoms and preferably 1 to 6 and unsaturated aldehydes 3 to 12 carbon atoms including aromatic species. Similarly, as to the alcohols, aliphatics having from 1 to 8 carbon atoms, preferably 1 to 3 can be employed as well as diols, unsaturated alcohols and aromatic alcohols.

Besides methacrolein, other aldehydes can be used, such as saturated aliphatic aldehydes, or alpha,beta-unsaturated aliphatic aldehydes including acrolein, crotonaldehyde and the like. Finally, aromatic aldehydes such as benzaldehyde can also be used. Alcohols other than methyl, such as ethyl, propyl, ethylene glycol, alkyl, benzyl and the like can also be used very effectively in the esterification process.

The conversion reaction can be conducted in a closed reaction vessel by combining the catalyst and reactants, alcohol and aldehyde, together and mixing for a period of time as has been exemplified hereinbelow. Alternatively, as will be appreciated by those skilled in the art, the reaction could also be conducted in either a fixed-bed or fluid-bed reactor at temperatures of from about 20° C. to about 200° C. and pressures of about 0.2 to about 10 atmospheres. The catalyst can be employed unsupported or supported on a carrier; suitable support materials include silica, alumina, boron-phosphate, titania, zirconia and the like and preferably Alundum as well as mixtures thereof. Alundum is a registered trademark of the Norton Co. for fused-alumina refractory materials. The catalyst can have any of the conventional fixed-bed forms such as coated, tablet, pellet, extruded, spherical, or fluid-bed forms such as microspherical or other forms known in the art. Presence of the catalyst increases the rate and percent of conversion per single pass.

Catalyst preparation is not a feature of the present invention but is described in detail in our copending application, Ser. No. 724,535, now U.S. Pat. No. 4,623,635 the subject matter of which is incorporated herein by reference. Nevertheless, for convenience, the compostion of the catalyst used in the esterification process of this invention shall be set forth herein. Specifically, in the foregoing catalyst formula, the optional promoter elements are preferably Te and Zn, and of group E, preferably Al, Pb, Sn, Sb, As, Cu, Ag, Au and Fe.

The effectiveness of the catalyst system disclosed herein and its use to esterify aldehydes, such as methacrolein, with alcohols, was determined and calculated by measuring the percent conversion yield as follows:

$$\text{Percent Conversion} = \frac{\text{Moles of product recovered}}{\text{Moles of aldehyde fed}} \times 100$$

The esterification procedure utilized in the practice of this invention has collective advantages that are significant. A solid catalyst system which is readily handled and recovered from the produced ester is utilized; the invention process is effective under mild conditions of temperature, pressure and time of reaction; good percent per pass conversion in a direct one-step procedure is also achieved.

Catalyst Preparation

The palladium based catalyst that can be utilized in the practice of the esterification process of this invention can be prepared as follows:

Palladium chloride (0.886 g) was placed in a 300 cc beaker and 50 cc diluted HCl (3.0 cc) was added. The suspension was heated to 60° C. for 30 minutes after which all of the palladium chloride was dissolved. Zinc nitrate as [Zn(NO$_2$)$_2$.6H$_2$O] (0.373 g) in 5 cc of H$_2$O was added to the palladium solution. Then TeO$_2$ (0.199 g) was added and the mixture was stirred for 15 minutes. After that period of time, 10 cc of formalin was added to the solution. Diluted KOH solution was added to adjust the pH to 7.5. A black percipitant was formed. The mixture was stirred for 1 hour before filtration. The precipitant was washed with 1.0 liter of water, and was dried in the oven at 110° to 120° C. over night.

Other selected catalysts can be prepared in the same manner by employing the appropriate metal salts as is true for Examples No. 2 through 8; this can be done within routine expertise. Alternatively, other methods for catalyst preparation can also be employed.

EXAMPLE NO. 1

0.15 g of catalyst of the following catalyst composition, PdTe$_{0.25}$Zn$_{0.25}$, was placed ina 20 cc vial containing a magnetic stirrer and the vial was then sealed. The vial was flushed with oxygen for 15 minutes and then 2 g of methanol and 0.2 g of methacrolein were introduced into the vial. The mixture was stirred at room temperature for approximately 16 hours and subsequently analyzed. The per pass conversion to methyl methacrylate was 50.5 percent.

EXAMPLE NOS. 2-8

Other palladium alloys were employed in the same manner as set forth for Example No. 1 for the esterification of methacrolein with methanol. These include Examples No. 2 through 8, reported in Table I hereinbelow. Product analysis was done in a Hewlett-Packard Model S110A gas chromatograph fitted with a flame ionization detector and a SP 1200 column.

EXAMPLE NOS. 9-12

Example Nos. 9 through 12 were prepared by different methods, namely, metal displacement (Nos. 9 and 11) and reduction with CH$_2$O/KOH (Nos. 10 and 12). Both methods are applicable to obtain a catalyst for use in the esterification process of this invention and are set forth in detail in our aforesaid copending application, U.S. Ser. No. 724,53, now U.S. Pat. No. 4,623,635, the subject matter of which is incorporated herein by reference. These four palladium alloys were also employed in substantially the same manner as set forth in Example No. 1. One difference was that the reaction temperature for Example Nos. 11 and 12 was 50° C. rather than room temperature.

EXAMPLE NO. 13

As a control, the preferred mode of Example 1 was repeated utilizing palladium metal as the sole catalyst.

TABLE I

Esterification of Methacrolein with Palladium Based Catalysts

| Example No. | Catalyst Metallic Composition | Conversion to Methylmethacrylate (MMA) |
|---|---|---|
| 1 | Pd$_{1.0}$Zn$_{0.25}$Te$_{0.25}$ | 50.5 |
| 2 | Pd$_{1.0}$Pb$_{0.25}$Te$_{0.25}$ | 31.3 |
| 3 | Pd$_{1.0}$Te$_{0.25}$Sb$_{0.25}$ | 4.2 |
| 4 | Pd$_{1.0}$Zn$_{0.25}$Pb$_{0.25}$ | 19.4 |
| 5 | Pd$_{1.0}$Zn$_{0.25}$ | 4.2 |
| 6 | Pd$_{1.0}$Te$_{0.25}$ | 3.6 |
| 7 | Pd$_{1.0}$Zn$_{0.25}$Sb$_{0.25}$ | 1.0 |
| 8 | Pd$_{1.0}$Pb$_{0.25}$ | 0 |
| 9 | Pd$_1$Zn$_1$ | 38.2 |
| 10 | Pd$_1$Zn$_1$ | 29.7 |
| 11 | Pd$_1$Zn$_2$ | 51.9 |
| 12 | Pd$_1$Zn$_2$ | 41.0 |
| 13 | Pd* | 5.6 |

From the results presented in Table I, it can be seen that the catalysts containing palladium, tellurium and zinc, or palladium, tellurium and lead, Nos. 1 and 2 performed very well. Palladium and tellurium, and palladium and zinc or lead catalysts (Example Nos. 5-8) were generally not effective, but palladium with zinc and lead performed fairly well. Actually, the catalysts in Examples 5-8 contained less than a sufficient amount of promoter metal as can be determined by considering the per pass conversions for Examples Nos. 9-12 where greater amounts of zinc were present as a result of different methods of preparation. Presumably, a more optimum palladium/tellurium or palladium/lead composition could also be employed in lieu of the compositions tried in Examples 6 and 8, respectively. Example No. 13, the comparative control, employed palladium metal alone.

While specific catalyst compositions may not be best suited for a particular esterification reaction, it is to be appreciated that there are combinations and proportions of promoter metals that will form highly useful catalysts for practice of the invention. Such determinations can be made readily by those of ordinary skill in the art without resort to undue experimentation.

Based upon the yields of methyl methacrylate that have been obtained when a palladium based catalyst has been employed according to the process of the present invention as set forth herein, it should be apparent that a one step esterification is possible. It is to be understood that the esterification process disclosed herein is applicable, in general, to palladium catalysts which, as stated hereinabove, include one or more promoters. So long as one promoter is present, the presence or absence of additional elements or compounds will not affect the process set forth herein.

It should be apparent to those skilled in the art that our invention is operable with palladium based catalysts having certain ratios of promoter metals to palladium and it is operable as various promoters and temperatures are varied. It is also operable with a wide variety of reactants, i.e., aldehydes and alcohols. It is to be understood that all of these variables fall within the scope of the claimed invention and that it is not to be limited by the examples which are representative and demonstrate operability; and furthermore, it is believed that the selection of specific reactants, promoters and reaction conditions can be determined without departing from the spirit of the invention herein disclosed and described, and that the scope of the invention includes all modifications including equivalents and variations falling within the scope of the attached claims.

We claim:

1. A process for the one step esterification of aldehydes and alcohols comprising the steps of:
   combining an aldehyde with an alcohol, in the presence of oxygen and in contact with a catalyst having the general formula $PdTe_aZn_d$ where a and d are from 0.25 to 3.

2. A process, as set forth in claim 1, wherein said aldehydes are selected from the group consisting of saturated aldehydes having from one to 12 carbon atoms and unsaturated aldehydes having from three to 12 carbon atoms including aromatic aldehydes.

3. A process, as set forth in claim 2, wherein said alcohols are selected from the group consisting of aliphatics having from one to 8 carbon atoms; diols, unsaturated alcohols and aromatic alcohols.

4. A process, as set forth in claim 3, wherein said aldehyde is acrolein and said alcohol is methanol.

5. A process, as set forth in claim 3, wherein said aldehyde is methacrolein and said alcohol is methanol.

6. A process, as set forth in claim 5, wherein said catalyst is $PdTe_{0.25}Zn_{0.25}$.

7. A process, as set forth in claim 3, wherein said aldehyde is acrolein, said alcohol is methanol and said catalyst is $PdTe_{0.25}Zn_{0.25}$.

8. A process, as set forth in claim 1, wherein said esterification is conducted at a temperature of from about 20° to 200° C. and an oxygen pressure ranging from subatmospheric to about 20 atmospheric.

9. A process, as set forth in claim 8, wherein said alcohol is combined with said aldehyde in a ratio of from about 1:1 to 50:1.

* * * * *